United States Patent
Cavallini et al.

(10) Patent No.: US 8,616,045 B2
(45) Date of Patent: Dec. 31, 2013

(54) METHOD AND DEVICE FOR DERIVING THE CONCENTRATION OF A GAS DISSOLVED IN AN ELECTRICAL INSULATION OIL

(75) Inventors: Andrea Cavallini, San Pietro in Casale (IT); Fabio Ciani, Forlì (IT); Stefano Serra, San Vittore Olona (IT); GianCarlo Montanari, Casalecchio di Reno (IT)

(73) Assignee: Techimp Technologies S.R.L., Bologna (IT)

( * ) Notice: Subject to any disclaimer, the term of this patent is extended or adjusted under 35 U.S.C. 154(b) by 16 days.

(21) Appl. No.: 13/521,271

(22) PCT Filed: Jan. 10, 2011

(86) PCT No.: PCT/IB2011/050077
§ 371 (c)(1), (2), (4) Date: Jul. 10, 2012

(87) PCT Pub. No.: WO2011/086479
PCT Pub. Date: Jul. 21, 2011

(65) Prior Publication Data
US 2012/0291521 A1    Nov. 22, 2012

(30) Foreign Application Priority Data
Jan. 14, 2010 (IT) .............................. BO2010A0016

(51) Int. Cl.
*G01N 33/30* (2006.01)
*G01N 33/26* (2006.01)

(52) U.S. Cl.
USPC ........................................................ 73/19.11

(58) Field of Classification Search
USPC ..................................... 73/19.1, 19.11, 19.12
See application file for complete search history.

(56) References Cited

U.S. PATENT DOCUMENTS 4,058,373 A * 11/1977 Kurz et al. ........................ 95/46
4,236,404 A * 12/1980 Ketchum et al. ............. 73/19.02
(Continued)

FOREIGN PATENT DOCUMENTS

WO       98/36265 A1    8/1998
WO  WO 03075294 A1 *  9/2003   .............. H01F 27/40

OTHER PUBLICATIONS

"Dissolved Gas Analysis Guide for Transformers Filled with Beta Fluid," DSI Ventures, Inc. 2006. <www.dsiventures.com>.*

(Continued)

*Primary Examiner* — Lisa Caputo
*Assistant Examiner* — Punam Roy
(74) *Attorney, Agent, or Firm* — Pearne & Gordon LLP

(57) ABSTRACT

A method for deriving the concentration of a gas dissolved in an electrical insulating oil (2) comprises the following steps:—preparing a membrane (5) permeable to the gas, interposed between a container (7) of the oil (2) and a measuring chamber (4) that receives a part of the gas through the membrane (5);—measuring the value of gas concentration in the measuring chamber (4);—deriving an estimated value of the concentration of the gas in the oil (2) as a function of the measured value,—the measuring step comprising taking at successive measuring instants a plurality of measurements of the values of gas concentration in the measuring chamber (4);—the deriving step comprising calculating the estimated value of gas concentration in the oil (2), at an instant selected from said measuring instants, according to a non-linear function of the values measured at the selected measuring instant and at one or more of the measuring instants preceding the one selected.

12 Claims, 2 Drawing Sheets

(56) References Cited

U.S. PATENT DOCUMENTS

| | | | |
|---|---|---|---|
| 4,444,040 A * | 4/1984 | Sakai et al. | 73/19.02 |
| 4,455,860 A * | 6/1984 | Cullick et al. | 73/19.11 |
| 4,763,514 A * | 8/1988 | Naito et al. | 73/19.11 |
| 4,890,478 A * | 1/1990 | Claiborne et al. | 73/19.11 |
| 4,944,178 A * | 7/1990 | Inoue et al. | 73/19.1 |
| 5,659,126 A | 8/1997 | Farber | |
| 6,037,592 A | 3/2000 | Sunshine et al. | |
| 6,289,716 B1 * | 9/2001 | Lindgren | 73/19.1 |
| 6,324,891 B1 * | 12/2001 | Gibeault et al. | 73/19.01 |
| 6,391,096 B1 * | 5/2002 | Waters et al. | 96/6 |
| 6,526,805 B1 * | 3/2003 | Babes-Dornea et al. | 73/19.12 |
| 6,968,728 B2 * | 11/2005 | Gilbert et al. | 73/19.12 |
| 6,974,705 B1 * | 12/2005 | Brumboiu et al. | 436/181 |
| 7,040,138 B2 * | 5/2006 | Braesel et al. | 73/19.01 |
| 7,747,417 B2 * | 6/2010 | Lamontagne | 702/188 |
| 8,224,600 B2 * | 7/2012 | Akiyama et al. | 702/65 |
| 8,347,687 B2 * | 1/2013 | Cunningham | 73/19.11 |
| 2002/0161558 A1 * | 10/2002 | Georges et al. | 702/189 |
| 2011/0246088 A1 * | 10/2011 | Santos | 702/24 |
| 2012/0290229 A1 * | 11/2012 | Cavallini et al. | 702/58 |

OTHER PUBLICATIONS

V. Duraisamy, N. Devarajan, D. Somasundareswari, A. Antony Maria Vasanth, S. N. Sivanandam, "Neuro fuzzy schemes for fault detection in power transformer," Applied Soft Computing, 7 Available online on Nov. 21, 2006. pp. 534-539.*

Z. Wang, "Artificial intelligence application in the diagnosis of power transformer," pHD Thesis, Virginia Polytechnic Institute and State University, 2000. Chapter 6, pp. 54-65.*

Rasmussen, M.L., Civan, F., "Parameters of Gas Dissolution in Liquids Obtained by Isothermal Pressure Decay", AICHE Journal, vol. 55, No. 1, Nov. 10, 2008, pp. 9-23.

* cited by examiner

METHOD AND DEVICE FOR DERIVING THE CONCENTRATION OF A GAS DISSOLVED IN AN ELECTRICAL INSULATION OIL

TECHNICAL FIELD

This invention relates to a method and a device for deriving the concentration of a gas dissolved in an electrical insulation oil.

More generally, this invention relates to a diagnostic method and apparatus for assessing the insulation condition of an insulating oil in an electrical apparatus.

The invention thus addresses the field of diagnostic assessment of oil-insulated electrical apparatuses such as transformers or cables.

BACKGROUND ART

Especially in the field of medium- or high-voltage transformers, oil is frequently used to insulate the transformer, for the reasons set out below.

Partial discharge is a well-known phenomenon in electrical apparatuses subjected to medium or high voltages.

A partial discharge is an electric discharge limited to a portion of the insulation of an electrical system and does not therefore cause immediate failure of the system but, more generally, causes its gradual degradation. By their very nature, therefore, partial discharges are substantially limited in extent to a defect in the insulating system.

In light of this, the use of a liquid insulator such as oil has the advantage of allowing convective movements within the oil and thanks to certain chemical processes, this type of insulation is at least partly self-restorative, that is to say, it is capable of at least partly compensating the degradation it undergoes during operation of the transformer.

It is known that partial discharges that take place in the oil cause gases to be formed.

Another factor in the evolution of gases is the reaching of very high temperatures by the oil.

For this reason, diagnostic systems based on the assessment of gas concentration in the oil have been in use for some time to assess the insulation condition of oil-insulated transformers.

In this field, the most advanced solutions involve the use of a membrane permeable to the gas, interposed between a container for the oil and a measuring chamber containing only gas. The measuring chamber receives through the membrane a part of the gas present in the oil.

That way, by separating the measuring chamber from the oil it is possible to place a sensor in the measuring chamber to measure the value of gas concentration in the measuring chamber. The sensor is particularly reliable because it is never in contact with the oil.

This type of configuration, however, makes it necessary to estimate the value of gas concentration in the oil as a function of the value measured in the measuring chamber. In effect, it is not the quantity of interest, namely, the gas concentration in the oil, that is measured directly but a quantity indirectly correlated with it, namely, the concentration of the gases inside the measuring chamber.

This estimated value is derived using suitable processing means which implement formulas that reflect the condition of equilibrium between the concentration of gases in the oil and the concentration of gases in the measuring chamber.

It should be observed, however, that these formulas do not take into account the dynamics of the phenomenon by which the gases pass through the membrane from the oil to the measuring chamber.

The aforesaid technical solutions therefore have certain shortcomings.

First of all, there is the risk that the values estimated for gas concentration in the oil will differ considerably from the real values. Typically, the risk is such that the values will be underestimated, leading to serious diagnostic assessment errors when the estimated values are interpreted.

Moreover, there is also the risk that such an estimation of the values of gas concentration in the oil will not allow particularly intense partial discharge phenomena to be identified at all or to be identified with an unacceptable delay. That makes such measuring systems somewhat unreliable for diagnostic purposes.

Lastly, the aforesaid prior art systems are not very precise or reliable during the steps of checking and adjusting (setting up) the devices themselves, where particularly rapid transients in the variation of gas concentration in the oil are created.

In effect, it should be observed that some prior art systems contemplate a calibration procedure to take into account the dynamics of the phenomenon by which gas passes through the membrane from the oil to the measuring chamber.

These calibration procedures involve setting a first predetermined value of gas concentration in the oil and measuring the corresponding value of gas concentration in the measuring chamber, then setting a second predetermined value of gas concentration in the oil (greater than the first value) and measuring the corresponding value of gas concentration in the measuring chamber, and so on.

That provides a plurality of experimental values of gas concentration in the to measuring chamber, each corresponding to a known value of gas concentration in the oil.

These experimental points are then interpolated to derive a coefficient of proportionality, that is to say, a coefficient of calibration.

These calibration procedures, however, are also not free of disadvantages because they are highly time-consuming and, in any case, involve a somewhat heavy approximation, with the result that estimation of the value of gas concentration in the oil is relatively imprecise.

It should also be observed that systems which involve measuring gas concentration in a measuring chamber separated from the oil by a membrane have a further drawback due to possible gas saturation in the measuring chamber.

In effect, if the concentration of the gas to be measured in the measuring chamber reaches saturation, the values measured by the sensor are not reliable.

To avoid saturation, it is necessary to discharge at least part of the gases present in the measuring chamber. This, however, leads to transients related to the transfer of the gases through the membrane, thus further increasing the risks of error in estimating the values of gas concentration in the oil, as described above.

DISCLOSURE OF THE INVENTION

This invention has for an aim to provide a method and a device for deriving the concentration of a gas dissolved in the electrical insulation oil of a transformer and which overcome the above mentioned disadvantages of the prior art.

More specifically, the invention has for an aim to provide a method and a device capable of deriving in a particularly precise and reliable way the concentration of a gas dissolved in the electrical insulation oil of a transformer.

Another aim of the invention is to provide a method and a device for deriving the concentration of a gas dissolved in the electrical insulation oil of a transformer without prior calibrations.

The method according to this invention comprises the following steps:
- preparing a membrane permeable to the gas, interposed between a container of the oil and a measuring chamber that receives a part of the gas through the membrane;
- measuring the value of gas concentration in the measuring chamber;
- deriving an estimated value of the concentration of the gas in the oil as a function of the measured value, The device according to this invention comprises:
- a membrane permeable to the gas, interposed between a container of the oil and a measuring chamber that receives a part of the gas through the membrane;
- a sensor mounted in the measuring chamber to measure a value of the gas concentration in the measuring chamber;
- processing means connected to the sensor to derive an estimated value of gas concentration in the oil according to the value measured in the measuring chamber.

These aims are fully achieved by the method of this invention, as characterized in the appended claims and, more specifically, in that:
- measuring comprises taking at successive measuring instants a plurality of measurements of the values of gas concentration in the measuring chamber;
- deriving comprises calculating the estimated value of gas concentration in the oil, at an instant selected from said measuring instants, according to a non-linear function of the values measured at the selected measuring instant and at one or more of the measuring instants preceding the one selected.

The device according to this invention is characterized in that the processing means are designed to take, at successive measuring instants, a plurality of measurements of the values of gas concentration in the measuring chamber and to calculate the estimated value of gas concentration in the oil at an instant selected from said measuring instants, according to a non-linear function of the values measured at the selected measuring instant and at one or more of the measuring instants preceding the one selected.

It should be observed that, preferably, the estimated value of gas concentration in the oil at an instant selected from said measuring instants, is calculated according to a non-linear function of the values measured at the selected measuring instant and at all the measuring instants preceding the one selected.

BRIEF DESCRIPTION OF THE DRAWINGS

These and other features of the invention will become more apparent from the following description of a preferred, non-limiting embodiment of it, with reference to the accompanying drawings, in which.

DETAILED DESCRIPTION OF THE PREFERRED EMBODIMENTS OF THE INVENTION

Figure 1:
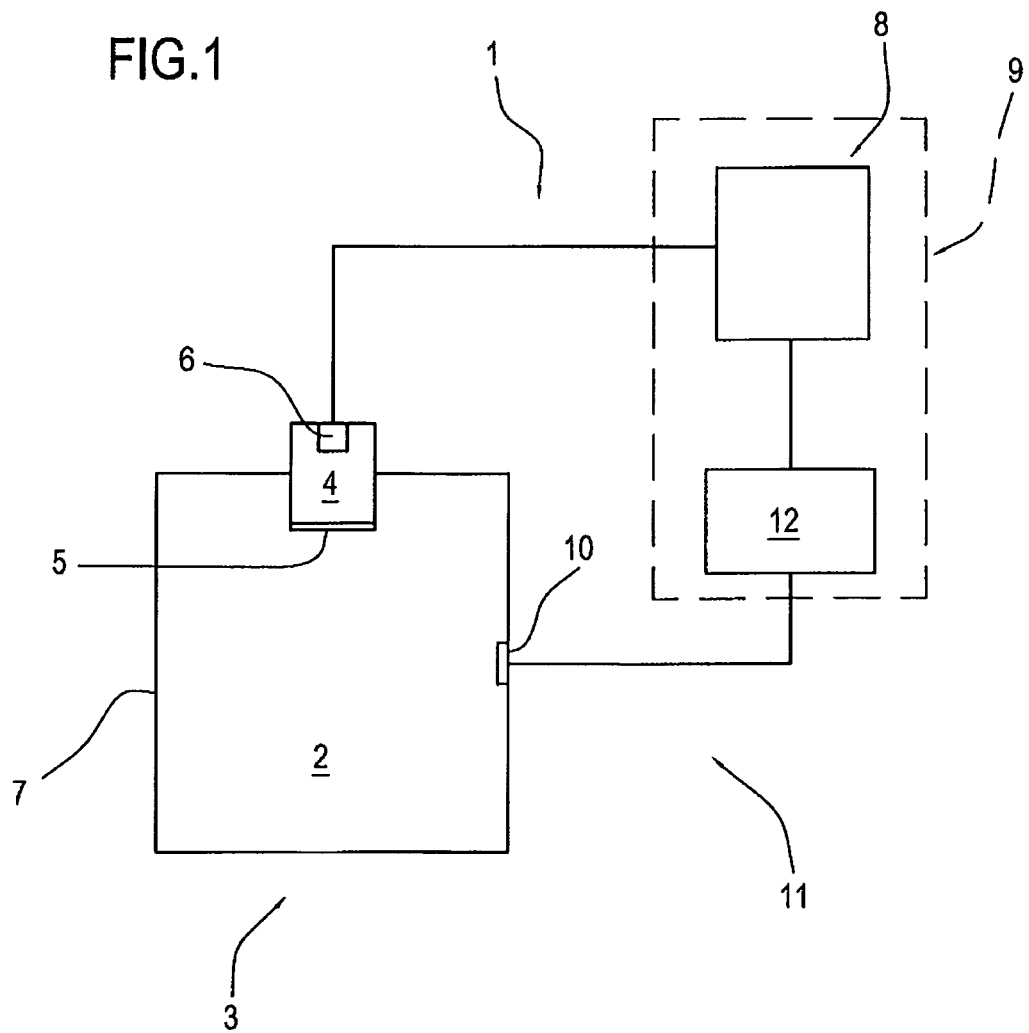
FIG. 1 schematically illustrates a device according to this invention.

The numeral 1 in FIG. 1 denotes a device according to this invention.

The device 1 is a device for deriving the concentration of a gas dissolved in insulation oil 2.

More specifically, the device 1 is a device for deriving the concentration of a gas dissolved in the insulation oil 2 of an electrical apparatus 3 (typically a transformer but possibly also a cable or other oil-insulated electrical apparatus).

Derivation of this kind is preliminary to analysis of the gases dissolved in the oil 2, called DGA (dissolved gas analysis).

As is known, this type of analysis (DGA) is used for diagnostic purposes for deriving information about the condition of the insulation of the electrical apparatus 3.

In effect, the gases dissolved in the oil 2 are generated by partial discharges that take place in the oil (or in parts of the electrical apparatus 3 subjected to the electric field and in contact with the oil 2) or by overheating of the oil 2. Both of these conditions constitute possible causes of a fault or in any case are a sign of risk for the operativeness of the electrical apparatus 3.

The electrical apparatus 3 comprises a container designed to hold the oil 2 and hereinafter referred to as container 7 of the oil.

The container 7 of the oil 2 also comprises a measuring chamber 4 containing only gas (for example, air).

The measuring chamber 4 is designed to receive from the container 7 of the oil the gas which evolved as a result of partial discharges or oil overheating.

The device 1 comprises a membrane 5 permeable to the gas and interposed between the measuring chamber 4 and the container 7 of the oil 2.

The membrane 5 allows the gas to pass through it from the container 7 of the oil to the measuring chamber 4 but prevents the oil 2 from passing through it from the container 7 of the oil to the measuring chamber 4.

The device 1 comprises a sensor 6 mounted in the measuring chamber 4 to measure the concentration of one or more gases in the measuring chamber 4.

The sensor 6 can measure the concentration of one or more predetermined types of gas, preferably, but not limited to, the following:
- carbon monoxide, hereinafter denoted CO;
- hydrogen, hereinafter denoted $H_2$;
- carbon dioxide, hereinafter denoted $CO_2$;
- acetylene, hereinafter denoted $C_2H_2$;
- ethylene, hereinafter denoted $C_2H_4$;
- methane, hereinafter denoted $CH_4$.

Alternatively, instead of a single sensor, the device 1 might comprise a plurality of sensors, each designed to measure the concentration of a predetermined type of gas.

The device 1 comprises a control unit 8 (or a processor or any other processing means) electrically connected to the sensor 6 to receive from the latter a signal corresponding to the value/values of concentration of the predetermined type/types of gas measured in the measuring chamber 4.

The control unit 8 comprises, preferably, but without limiting the scope of the invention, a memorization module (not illustrated) and a processing module (also not illustrated) functionally connected to the memorization module.

The control unit 8 defines processing means 9 configured to derive an estimated value of gas concentration in the oil 2, as a function of a corresponding value of gas concentration measured inside the measuring chamber 4.

Preferably, the device 1 also comprises a timer connected to the control unit 8 and designed to generate a signal which can be used by the processing module of the control unit 8 to generate (and memorize) measuring instants corresponding to the measurements taken by the sensor 6 in succession. The timer is connected to the control unit 8 also to allow a plurality of measurements (of the value of gas concentration in the measuring chamber 4) to be taken in succession at predetermined measuring instants.

The memorization module of the control unit 8 is designed to memorize the gas concentration values acquired by the sensor 6.

The control unit 8 associates a time information item, according to known techniques, with each acquired value of gas concentration in the measuring chamber 4, obtained, for example, by the timer and relating to the acquisition instant at which that gas concentration value is acquired.

For example, for each gas concentration value measured in the measuring chamber 4, the control unit 8 can memorize directly in the memorization module the time information item regarding the instant that value is acquired; and/or can sort the acquired values of gas concentration in the measuring chamber 4 according to a predetermined sequence and use a predetermined sampling step.

Hereinafter, the following notation will be used:

$t_i$ to denote a time instant;

$X_i$ to denote the value for the concentration of a predetermined gas inside the measuring chamber 4 measured by the sensor 6 at the time instant $t_i$;

$Y_i$ to denote the estimated value of gas concentration in the oil, calculated by the control unit 8;

$\bar{t}$ to denote a predetermined time interval;

$\bar{x}$ to denote a predetermined interval of variation of the gas concentration in the measuring chamber 4 preferably in the predetermined time interval $\bar{t}$;

K to denote the measurements taken (in the measuring time interval, not less than $\bar{t}$).

Express reference will hereinafter be made to the measurement of the concentration of a generic gas type inside the measuring chamber 4.

The method proposed can therefore be used to measure the concentration of any gas (or plurality of gases) inside the measuring chamber 4 and to estimate its concentration in the oil 2 accordingly.

The electronic control unit 8 acquires from the sensor 6, in a predetermined time interval T (where T is not less than $\bar{t}$), a plurality of values ($X_1, X_2, \ldots, X_k$) for the concentration of one predetermined type of gas inside the measuring chamber 4.

Preferably, the predetermined time interval $\bar{t}$ is approximately 24 hours.

Preferably, the concentration values ($X_1, X_2, \ldots, X_k$) measured inside the measuring chamber 4 are acquired at predetermined time intervals.

More specifically, preferably, but without limiting the scope of the invention, the gas concentration values ($X_1, X_2, \ldots, X_k$) measured inside the measuring chamber 4 are spaced at a constant time interval, that is to say, these concentration values ($X_1, X_2, \ldots, X_k$) are acquired by the control unit 8 preferably with a constant sampling step.

This advantageously simplifies subsequent processing of the measured concentration values by the control unit 8.

The concentration values ($X_1, X_2, \ldots, X_k$) measured inside the measuring chamber 4 are spaced preferably at a time interval of 15-25 minutes, and still more preferably, approximately twenty minutes.

According to the invention, however, the concentration values ($X_1, X_2, \ldots, X_k$) measured inside the measuring chamber 4 might also be spaced at non-constant time intervals, that is to say, these concentration values ($X_1, X_2, \ldots, X_k$) might be acquired by the control unit 8 with a sampling step that is not constant.

Figure 2:
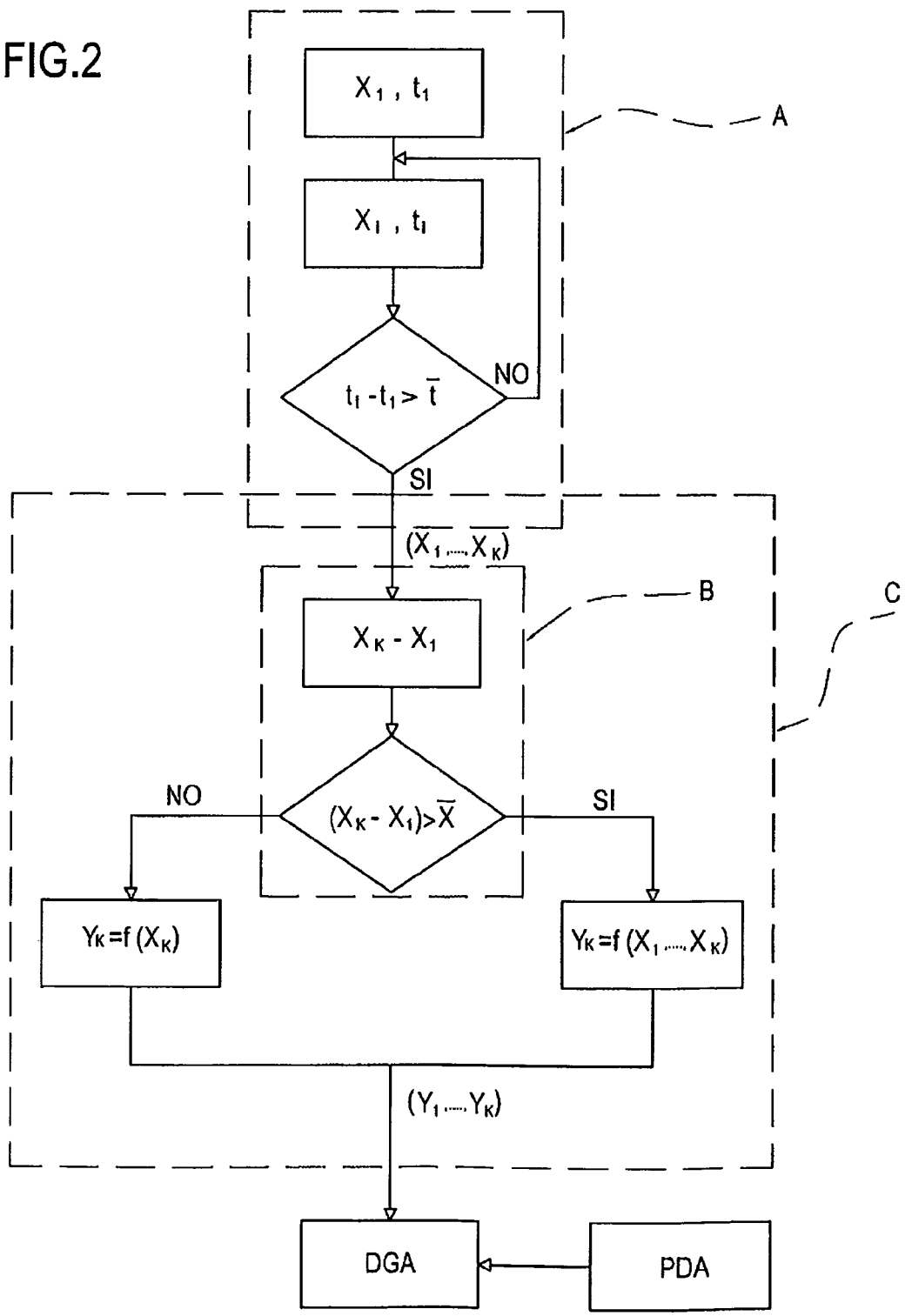
FIG. 2 schematically illustrates a method according to this invention.

At each acquisition of a concentration value $X_i$ in the measuring chamber 4, the control unit 8 checks whether $(t_i-t_1) > \bar{t}$, that is to say, whether or not the predetermined time interval $\bar{t}$ has passed from the time the first sample $X_1$ was acquired, as illustrated in the block A of the schematic diagram of FIG. 2.

It should therefore be observed that the acquisition time interval T, equal to $t_k-t_1$, is not less than the predetermined time interval $\bar{t}$.

The first value acquired after the period $\bar{t}$, $X_k$, is compared, preferably but without limiting the scope of the invention, with the very first value acquired, $X_1$.

Alternatively, the first value $X_k$ acquired after the predetermined time interval $\bar{t}$, might be compared with one or more of the previously acquired values $X_1 + X_{k-1}$.

This comparison is a comparison of the threshold type, that is to say, the difference ($X_k - X_1$) is compared with a predetermined interval $\bar{x}$ of variation of the gas concentration in the measuring chamber 4.

If the difference ($X_k - X_1$) is greater than the predetermined interval $\bar{x}$ of variation of the gas concentration in the measuring chamber 4, the estimated value $Y_k$ for the gas concentration in the oil corresponding to the value $X_k$ is derived by means of a non-linear function of the value $X_k$ and of the gas concentration values ($X_1, X_2, \ldots, X_{k-1}$) previously measured in the measuring chamber 4, that is to say, a non-linear function of the $Y_k = f(X_1, X_2, \ldots X_k)$ type.

It should be noted that this check is also carried out for any other value $X_i$ acquired after the first ($X_1$), as described above.

In effect, exceeding the predetermined interval $\bar{x}$ of variation of the gas concentration in the measuring chamber 4 indicates that a more or less sudden variation in the gas concentration in the oil 2 of the electrical apparatus 3 is in progress and, hence, that a transient of gas transfer through the membrane 5 is in progress.

Under these conditions it is very likely that an equilibrium has not yet been reached between the gas concentration in the oil 2 and the gas concentration inside the measuring chamber 4, on account of the dynamics of the phenomenon by which the gas passes through the membrane 5 from the oil 2 to the measuring chamber 4.

This non-linear function is also used to estimate the gas concentration in the oil for all the concentration values ($X_1, X_2, \ldots$) measured after the first (after finding that the difference ($X_i - X_1$) is greater than the predetermined value $\bar{x}$).

Preferably, the non-linear function (which links a predetermined gas concentration measured in the chamber 4 to the corresponding concentration of the same gas in the oil 2 in the container 7) is the function shown below by way of an example for the gas concentration value $X_k$ acquired in the measuring chamber 4 corresponding to a selected measuring instant $t_k$.

$$Y_k = \frac{(X_k - X_1 e^{-R_d t_k})}{R_d \lambda(T_g, P) \mathrm{erfc}\left(\frac{d}{\sqrt{4 D_i t_k}}\right)} - \frac{e^{-R_d t_k} \int^{k-1} dt' X(t') \mathrm{erfc}\left(\frac{d}{\sqrt{4 D_i t'}}\right) e^{R_d t'}}{\mathrm{erfc}\left(\frac{d}{\sqrt{4 D_i t_i}}\right)}$$

Where:

$\lambda(T_g, P)$ is Ostwald's solubility coefficient, which is a function of temperature and pressure, $$\text{erfc}\left(\frac{d}{\sqrt{4D_i t}}\right)$$

is the complementary error function, and

Rd and Di are experimental constants calculated on the basis of the polymer the membrane is made of.

The estimated value of gas concentration in the oil, $Y_k$, is calculated by the control unit 8, and more specifically, by the processing module.

Advantageously, the aforesaid non-linear function takes into account:

the dynamics of the process of gas diffusion through the membrane 5, this diffusion process being relatively slow;

the process of absorption and de-absorption of the gas through the membrane 5.

The aforesaid non-linear function therefore takes into account the transient of gas permeation through the membrane 5 in the predetermined time interval $\bar{t}$.

Thus, the device 1 advantageously makes it possible to derive, with a high degree of accuracy, the value of gas concentration in the oil 2; more specifically, the device 1 makes it possible to obtain a good estimation of the gas concentration in the oil 2 even for relatively slow gas-oil system transients.

Further, advantageously, the device 1 does not require complex calibrations to correlate the value $X_k$ (that is, any measured value $X_i$) of gas concentration inside the measuring chamber 4 with the value of gas concentration in the oil, as was the case with the prior art devices.

This reduces the setting up time of the device 1 and also decreases the risk of underestimating the value of gas concentration in the oil, in particular when the gas-oil system is far from its thermodynamic equilibrium.

Further, if the gases reach the saturation condition inside the measuring chamber 4, they can be discharged at least partly without diminishing the reliability of the gas concentration measurements performed by the device 1.

In effect, even if transients of gas transfer through the membrane 5 are triggered by the discharge of the gases, the device 1 is able to correctly estimate the value of gas concentration in the oil by means of the non-linear function.

The method for deriving the concentration of a gas dissolved in oil preferably contemplates, when the control unit 8 detects that $(X_k - X_1)$ is less than the predetermined value or interval $\bar{x}$ (that is, when $X_i - X_1$ is less than $\bar{x}$, for each i between 2 and k) of variation of the gas concentration in the measuring chamber 4, deriving the estimated value for the gas concentration in the oil corresponding to the value $X_i$ by means of a simplified linear function for the concentration value $X_i$, that is to say, by means of a linear function of the $Y_i = f(X_i)$ type.

In effect, not exceeding the predetermined interval $\bar{x}$ of variation of the gas concentration in the measuring chamber 4 indicates a situation of small variation of the gas concentration in the oil 2 in the electrical apparatus 3, which in turn indicates a condition of substantial equilibrium of the gas-oil system.

Thus, when the predetermined value or interval $\bar{x}$ of variation of the concentration is not exceeded, the device 1 uses that linear function advantageously to reduce the computational load of the control unit 8 and to simplify the calculation of the estimated value of the gas concentration in the oil.

Shown below is the linear function preferably used to calculate the estimated value $Y_i$ of gas concentration in the oil from the measured value $X_i$ of gas concentration in the measuring chamber 4.

$$Y_i = \lambda(T_g, P) \cdot X_i$$

Where:

$\lambda(T_g, P)$ is Ostwald's solubility coefficient.

The method for deriving the concentration of a gas dissolved in oil, illustrated schematically in FIG. 2, is preferably implemented with FIFO logic (that is, the first data item in is the first data item out of the block) with reference to the block C.

In effect, the first estimated value $Y_1$ of gas concentration in the oil calculated by the control unit using the linear or non-linear function corresponds preferably to the first value $X_1$ of gas concentration acquired in the measuring chamber 4, and so on for the remaining values.

The description set out above thus defines a method for deriving the concentration of a gas dissolved in an electrical insulating oil 2 of an electrical apparatus, comprising the following steps:

preparing a membrane 5 permeable to the gas, interposed between a container 7 of the oil 2 and a measuring chamber 4 that receives a part of the gas through the membrane 5;

measuring the value of gas concentration in the measuring chamber 4;

deriving an estimated value of the concentration of the gas in the oil 2 as a function of the measured value, characterized in that:

measuring comprises taking at successive measuring instants a plurality of measurements of the values of gas concentration in the measuring chamber 4;

deriving comprises calculating the estimated value of gas concentration in the oil 2, at an instant selected from said measuring instants, according to a non-linear function of the values measured at the selected measuring instant and at one or more of the measuring instants preceding the one selected.

Preferably, the plurality of measurements at successive measuring instants are taken in a predetermined measuring time interval within which the measurements can be ordered sequentially from a first measurement to a last measurement.

The method preferably comprises, after at least one of the measurements taken after the first, comparing that measured value with at least one of the values preceding the plurality of measured values.

The step of deriving the estimated value of the gas concentration in the oil 2 corresponding to that measurement is performed in a mode selected according to said comparing step from the following alternatives:

a calculation according to a non-linear function of the values measured at the selected measuring instant and at one or more of the measuring instants preceding the one selected, or a simplified calculation according to a linear function of the value measured at said selected measuring instant.

According to this invention, the diagnostic apparatus 11 further comprises a measurement module 10 for measuring electric pulses relating to partial electric discharges (hereinafter also referred to as PD, the abbreviation of the term Partial Discharges) which occur in the apparatus 3 (more specifically, in the transformer 3), and a processing unit 12.

It should be noted that the control unit 8 and the processing unit 12 can be integrated in a single processing unit; in any case, the control unit 8 and the processing unit 12 define the processing means 9.

More specifically, but not necessarily, the measurement module 10 for measuring electric pulses is of the electrical type (alternatively, it might be of optical or acoustical type); the measurement module 10 is configured to measure the current pulses that travel a measuring circuit coupled with the electrical system, of the transformer 3.

The processing unit 12 is connected to the device 1 and to the measurement module 10 for measuring the partial discharges. The processing unit 12 (integrated in the control unit 8 or connected to it) is designed to derive at least one concentration parameter correlated with the gas concentration measured in a predetermined acquisition time interval and at least one discharge parameter correlated with the partial discharges measured concurrently with the same acquisition time interval.

In particular, as regards the expression "concurrently" the following should be noted.

The expression "concurrently" is used to mean that the electrical discharges the discharge parameter is correlated with might be measured in the same acquisition time interval in which the gas concentration is measured or immediately before or after that time interval, that is to say that the discharges do not necessarily have to be acquired in the same time interval in which the gas concentrations are acquired, but might also be acquired before or after that time interval, provided always that gas and PD measurement times are sufficiently close to guarantee that the measured data relating to the gas concentrations and PD signals are pertinent to the same sources.

In effect, it should be observed that, generally speaking, a defect in the insulation of the apparatus 3, is at once a source of gas and a source of partial electric discharges (often, the discharges themselves, which occur in the oil or paper insulation, generate the gas).

The processing unit 12 comprises an identification module (not illustrated) connectable to a database containing reference values of predetermined indicators relating to a data set consisting at least of the concentration and discharge parameters.

These reference values of predetermined indicators contained in the database are characteristic values of predetermined categories of sources which generate the partial discharges and/or the gas dissolved in the oil.

The identification module is programmed to compare a data set composed of the values of the concentration and discharge parameters, derived by the processing unit 12, with the data in the database in order to assign that data set to one or more of those predetermined categories of sources which generate partial discharges and/or gas dissolved in the oil.

Preferably, the apparatus 11 also comprises display means (not illustrated), for example a display unit, connected to the processing unit 12 and designed to display the diagnostic indication regarding the identified sources of partial discharges and/or gas dissolved in the oil.

The operation of the diagnostic apparatus 11 is described below.

The device 1 measures the concentration of at least one gas dissolved in the insulating oil in the electrical apparatus 3 (in the manner described above).

More specifically, the device 1 measures the concentrations of CO and $H_2$ in the oil in a predetermined time interval and transmits these concentrations to the processing unit 12.

The processing unit 12 derives at least one concentration parameter as a function of the measured concentration of the at least one gas dissolved in the oil.

Preferably, the processing unit 12 derives the following two concentration parameters:
the value of CO concentration in the oil;
and the value of $H_2$ concentration in the oil.

The measurement module 10 measures the electrical pulses relating to partial electrical discharges which occur in the oil and which generate the pulses.

More specifically, it is assumed that the transformer is subjected to alternating voltage; in light of this, it is possible to attribute to each electrical pulse (partial discharge) measured, the value of a phase parameter, given by the phase (or the value) of the voltage applied to the transformer (or to the electrical apparatus 3) at the instant in which the pulse is measured.

Preferably for each pulse measured, the processing unit 12 extracts the value of parameters correlated with the waveform of the pulse.

More specifically, for each of the pulses measured, the processing unit 12 derives the following:
the value of an amplitude parameter correlated with the amplitude of the pulse measured;
the value of a phase parameter, representing the value of an alternating voltage applied to the electrical apparatus at the instants of measuring the pulses;
the value of a first shape parameter W correlated with the frequency content of the pulse;
and the value of a second shape parameter T, correlated with the duration of the pulse.

It should be noted that, for deriving the above mentioned shape parameters T and W, the processing unit 12 is preferably programmed to operate as follows:
the first shape parameter W is derived as standard deviation of the partial discharge pulse processed in the frequency domain;
the second shape parameter T is derived as standard deviation of the partial discharge pulse processed in the time domain.

The processing unit therefore creates a data set comprising, for each of the pulses measured, the value of the aforesaid shape parameters T and W, of the amplitude parameter, correlated with the amplitude of the pulse measured, and the value of the phase parameter, representing the value of an alternating voltage applied to the electrical apparatus at the instants of measuring the pulses.

Preferably, the processing unit 12 processes the data set in order to attribute the activity of partial discharges relating to that data set to one or more categories correlated with the nature of the source of the partial discharges, preferably selected from the following categories:
internal,
surface,
corona.

It is specified that the expression "correlated with the nature of the source of the partial discharges" means that the categories represent the distribution of the electric field within the space region (of the defect that generates the partial discharges) where the PD occur; in effect, it should be observed that the partial discharge activity (that is, the dimension, phase and time sequence of the partial discharges that occur in sequence in a reference time interval) is closely correlated with the distribution of the electric field in the region where the discharges occur.

The "internal" category relates to an activity of partial discharges which occur in the air gaps delimited by dielectric surfaces, or dielectric solids and metal electrodes, and which have a significant component of the electric field at right angles to the surfaces (fixed gaps).

The "surface" category relates to an activity of partial discharges involving the surfaces of solid and/or liquid insulating materials and which have a significant component of the electric field tangential to the discharge surfaces.

The "corona" category relates to an activity of partial discharges which occur in air starting from a pointed element.

Preferably, the processing unit 12 compares the data of the set comprising the amplitude and phase parameters of the measured pulses with reference data contained in a database and relating to reference values adopted by the amplitude and phase parameters for the aforesaid categories of sources which generate partial discharges (that is to say, internal, surface and corona).

It should be observed that the attribution of the measured discharge activity (that is, the attribution of the measured data set) to the internal/surface/corona categories occurs by processing the data relating to the phase and amplitude of the discharges measured; preferably, this processing consists of assessing the phase-amplitude pattern associated with that data set; more specifically, the assessment is performed preferably using a fuzzy inference engine.

The attribution of the measured data set to the phase and amplitude parameters of the measured pulses to the aforesaid categories of partial discharge sources constitutes a discharge parameter.

Preferably, the processing unit 12 derives the following discharge parameters:

an indication of presence or absence of partial discharges in the apparatus 3 (that is, in the transformer);

an indication of presence of intermittent partial discharges in the apparatus 3 (that is, in the transformer);

an attribution of the partial discharges measured (that is, data sets relating to a plurality of PD measured) to the internal, surface and corona categories.

Thus, the processing unit 12 defines the identification module which identifies the type of apparatus insulation defect that generates the partial discharges and/or the gases dissolved in the oil.

The identification module of the processing unit 12 compares the data set composed of the values of the concentration and discharge parameters with the reference values of predetermined indicators relating to the concentration and discharge parameters contained in the database in order to attribute that data set to one or more of those predetermined categories of sources of partial discharges and/or gas.

That allows the type of source that generates the partial discharges and/or the gas dissolved in the oil to be identified from among one or more predetermined categories of partial discharges and/or gas.

More specifically, reference will be made below to the case where the apparatus 3 consists of a transformer.

The diagnostic apparatus 11 is configured to identify the source (or one or more of the sources) which generate partial discharges and/or gas dissolved in the oil in a transformer from among the categories of sources listed below:

overheating of the transformer;

electric arcing in a core of the transformer;

defects in paper insulation of the transformer;

electrical discharges produced in the oil by a high voltage electrode of the transformer;

electrical discharges in poorly impregnated zones inside the transformer;

oil bubbles;

discharges produced along an outside surface of the transformer insulation.

The processing unit 12 attributes the derived concentration and discharge parameter data set to the category "overheating of the transformer" if the value of CO concentration in the oil is greater than the corresponding reference value, present in the database, and in the absence of partial discharges in the transformer.

The predetermined database reference value for CO concentration takes into account the CO concentration in the oil under optimum working conditions of the transformer, that is to say, when the transformer is not overheated.

Preferably, the predetermined database reference value for CO concentration is 1500 ppm.

More preferably, the predetermined database reference value for CO concentration is 400 ppm.

The processing unit 12 attributes the derived concentration and discharge parameter data set to the category "electric arcing in a core of the transformer" if the value of $H_2$ concentration in the oil is greater than a corresponding first reference value, corresponding to a "high" concentration of $H_2$, and in the absence of partial discharges.

Preferably, the corresponding first reference value for $H_2$ concentration, corresponding to a "high" concentration of $H_2$, is 10000 ppm.

That corresponding first reference value relates to a "high" concentration of $H_2$ in the oil.

The processing unit 12 attributes the derived concentration and discharge parameter data set to the category "electrical discharges produced in the oil by a high voltage electrode of the transformer" if the value of $H_2$ concentration in the oil is greater than the corresponding first reference value, corresponding to a "high" concentration of $H_2$, and in the presence of an activity of partial discharges attributed to the corona category.

Preferably, the corresponding first reference value for $H_2$ concentration, corresponding to a "high" concentration is 10000 ppm.

The processing unit 12 can use as further discharge parameters also the T and W shape parameters to attribute the data set to the category "electrical discharges produced in the oil by a high voltage electrode" so as to derive the diagnostic indication with a higher degree of reliability.

In effect, the aforesaid derived T and W shape parameters have, values which are, respectively, greater than a predetermined reference value (T "high") and lower than another predetermined reference value (W "low") when the source of partial discharges and/or gas are electrical discharges produced in the oil by a high-voltage electrode.

Preferably, the predetermined reference value for T is 5 mS, while the predetermined reference value for W is 1 Mhz.

The aforesaid reference values for T and W (5 ms and 1 Mhz) apply when the signals relating to the electric pulses are carried in a passband typical of a capacitive coupler.

The processing unit 12 attributes the derived concentration and discharge parameter data set to the category "defects in paper insulation of the transformer" if the value of $H_2$ concentration in the oil is greater than a corresponding reference value, relating to a "low" concentration of $H_2$ in the oil, and in the presence of intermittent partial discharges.

Preferably, the corresponding reference value for $H_2$ concentration, corresponding to a "low" concentration of $H_2$, is 200 ppm.

The processing unit 12 attributes the derived concentration and discharge parameter data set to the category "electrical discharges in poorly impregnated zones inside the transformer" if the value of $H_2$ concentration in the oil is greater than the corresponding reference value, relating to a "high" concentration of $H_2$, and in the presence of an activity of partial discharges attributed to the internal and/or surface category.

The processing unit 12 can use as further discharge parameters also the T and W shape parameters to attribute the data set to the category "electrical discharges in poorly impregnated zones inside the transformer", so as to derive the diagnostic indication with a higher degree of reliability.

In effect, the aforesaid derived T and W shape parameters have, values which are, respectively, greater than a predetermined reference value and lower than another predetermined reference value when the source of partial discharges and/or gas are electrical discharges in poorly impregnated zones inside the transformer.

Preferably, the predetermined reference value for T is 5 mS, while the predetermined reference value for W is 1 Mhz.

The aforesaid reference values for T and W (5 ms and 1 Mhz) apply when the signals relating to the electric pulses are carried in a passband typical of a capacitive coupler.

The processing unit 12 attributes the derived concentration and discharge parameter data set to the category "oil bubbles" in the transformer if the value of $H_2$ concentration in the oil is less than the corresponding reference value, relating to a "low" concentration of $H_2$ in the oil, and in the presence of an activity of partial discharges attributed to the internal and/or surface category.

Preferably, the corresponding reference value for $H_2$ concentration, corresponding to a "low" concentration of $H_2$, is 200 ppm.

Further, when the processing unit 12 attributes the derived concentration and discharge parameter data set to the category "oil bubbles", the degree of belonging of the data set comprising the discharge parameters to the categories correlated with the nature of the partial discharge source (internal, surface, corona) is highest for the "internal" category.

The processing unit 12 attributes the derived concentration and discharge parameter data set to the category "electrical discharges produced along an outside surface of the transformer insulation" if the value of $H_2$ concentration in the oil is less than a first corresponding reference value, relating to a "high" concentration of $H_2$ in the oil and greater than a second corresponding reference value, relating to a "low" concentration of $H_2$ in the oil and in the presence of an activity of partial discharges attributed to the internal and/or surface category.

Preferably, the first reference value for $H_2$ concentration, corresponding to a "high" concentration of $H_2$, is 10000 ppm, and the second reference value for $H_2$ concentration, corresponding to a "low" concentration of $H_2$, is 200 ppm.

Further, when the processing unit 12 attributes the derived concentration and discharge parameter data set to the category "electrical discharges produced along an outside surface of the transformer insulation", the degree of belonging of the data set comprising the discharge parameters to the categories correlated with the nature of the partial discharge source (internal, surface, corona) is highest for the "surface" category.

Table 1 below shows the attribution of the sources of partial discharges and/or gas as a function of the values of the concentration parameter/s and of the discharge parameter/s using the diagnostic method and the diagnostic apparatus of this invention.

TABLE 1

|  |  | PDA | | | |
|---|---|---|---|---|---|
|  |  | absence of PD | intermittent PD | corona PD | internal-surface PD |
| DGA | concentration of H2 greater than a predetermined value (high) | electric arcing in a core |  | electrical discharges from a high voltage electrode | electrical discharges in non-impregnated zones inside the transformer |
|  | concentration of H2 between two predetermined values (medium) |  |  |  | discharges along an outside surface of the transformer |
|  | concentration of H2 less than a predetermined value (low) |  |  | defects in paper insulation | oil bubbles |
|  | Presence of CO |  | overheating of the transformer; |  |  |

The processing unit 12 may further comprise a filtering module, that is, a filter, configurable to select only a part of the electrical pulses relating to partial discharges measured in the acquisition time interval so as to derive the discharge parameter only on the selected part of the partial discharges.

For example, the filter allows the processing unit 12 to derive one or more discharge parameters correlated with the partial discharges and excluding electrical discharges due to predetermined types of noise, so as to advantageously derive discharge parameters which are reliable and immune to noise.

The diagnostic apparatus 11 advantageously makes it possible to obtain highly reliable diagnostic indications regarding the insulation state of an electrical apparatus, in particular a transformer.

In effect, the diagnostic apparatus 11 derives a diagnostic indication about the insulation conditions of an electrical apparatus by combining DGA with PDA.

Thus, the apparatus 11 proposed is particularly robust against uncertainty of measured data, as regards both DGA and PDA.

In effect, according to the invention, to perform a reliable diagnosis (with an excellent capacity of discernment to distinguish the type of defect) it is sufficient to measure the gases (CO e $H_2$) with the highest concentrations (and thus particularly easy and reliable to measure) and from there derive indications on the nature of the PD sources.

Compared to DGA based prior art diagnostic apparatuses, this diagnostic apparatus can provide a higher number of diagnostic indications by measuring the concentration in oil of a smaller number of gases, with obvious advantages in terms of costs and operating reliability of the diagnostic apparatus.

Furthermore, unlike the case of prior art DGA solutions, any errors in estimating the concentration of one or more gases in the oil do not significantly reduce the reliability of the diagnostic indications derived by the apparatus 11; in effect, the diagnostic information is derived using at least one concentration parameter obtained by DGA and at least one discharge parameter obtained by PDA.

Advantageously, therefore, the sensors used in the diagnostic apparatus 11 to measure the concentration of gases in the oil may be less precise and accurate than those of the prior art, DGA based apparatuses, with obvious advantages in terms of costs.

Another advantage of this invention is that it provides a diagnostic apparatus 11 that can identify in a transformer a plurality of sources which generate partial discharges and/or gas dissolved in the oil with a high degree of discernment to distinguish these sources but without complicating the apparatus.

Moreover, the diagnostic apparatus of the invention uses a fuzzy inference engine operating on the concentration and discharge parameter to derive the aforesaid diagnostic indication.

The fuzzy inference engine makes it possible to attribute the data set composed of the values of the concentration and discharge parameters to one or more categories of sources which generate partial discharges and/or gas dissolved in the oil using predetermined rules applied to the concentration and discharge parameter/parameters.

This advantageously allows even more accurate diagnostic indications to be obtained, including an indication about the certainty (or uncertainty) of the indication provided, usually referred to by the term "likelihood".

In other embodiments of the diagnostic apparatus, other diagnostic indications about the insulation conditions of a transformer are derived on the basis of a data set consisting of a combination of one or more concentration parameters and one or more discharge parameters from among those set out above.

In any event, the data set comprising at least one concentration parameter and one discharge parameter must include a combination of concentration and discharge parameters from which at least one of the above mentioned sources of electrical discharges and/or gas must be identifiable.

Moreover, the apparatus 11 can derive further concentration and discharge parameters to improve the reliability of the diagnostic indications derived therefrom compared to those described above.

The description set out above also defines a diagnostic method for assessing the insulation condition of an electrical apparatus 3 insulated in oil 2, comprising the following steps:
  measuring the concentration of at least one gas dissolved in the insulating oil 2 in the electrical apparatus 3;
  deriving at least one concentration parameter correlated with the gas concentration measured in a predetermined acquisition time interval,
  measuring electrical pulses relating to partial electrical discharges which occur in the electrical apparatus 3 and which generate said pulses;
  deriving at least one discharge parameter correlated with the partial discharges measured substantially concurrently with said predetermined acquisition time interval;
  deriving a diagnostic indication about the insulation condition of the electrical apparatus 3 according to the derived values of the combined concentration and discharge parameters.

Preferably, in this method, the step of deriving the diagnostic indication comprises the following steps:
  preparing a database containing reference values of predetermined indicators relating to a data set comprising at least said concentration and discharge parameters, said reference values being characteristic of predetermined categories of sources that generate the partial discharges and/or the gas dissolved in the oil;
  comparing a data set composed of derived values of the concentration and discharge parameters with the data in the database in order to assign said data set to one or more of said source categories, thereby identifying the type of source that generates the partial discharges and/or the gas dissolved in the oil.

In another embodiment of the diagnostic method, the step of comparing a data set composed of derived values of the concentration and discharge parameters with the data in the database in order to assign said data set to one or more of said source categories is performed in order to provide a signal regarding the insulation condition of the electrical apparatus 3.

The signal may comprise information regarding the state of the insulation (for example, a traffic light which is green if the state of the insulation is good or red if the insulation is not in good condition and the electrical apparatus requires attention) or it may comprise information regarding the operation to be carried out on the transformer.

Further, in yet another embodiment of the diagnostic method, the step of deriving a diagnostic indication comprises using a fuzzy inference engine operating on the at least one concentration parameter and on the at least one discharge parameter in order to derive said diagnostic indication.

It will be understood that the invention described is susceptible of industrial application and may be modified and adapted in several ways without thereby departing from the scope of the inventive concept. Moreover, all the details of the invention may be substituted by technically equivalent elements.

The invention claimed is:

1. A method for deriving the concentration of a gas dissolved in an electrical insulating oil (2) of an electrical apparatus, comprising the following steps:
  preparing a membrane (5) permeable to the gas, interposed between a container (7) of the oil (2) and a measuring chamber (4) that receives a part of the gas through the membrane (5);
  measuring the value of gas concentration in the measuring chamber (4);
  deriving an estimated value of the concentration of the gas in the oil (2) as a function of the measured value, characterized in that:
  measuring comprises taking at successive measuring instants a plurality of measurements of the values of gas concentration in the measuring chamber (4);
  deriving comprises calculating the estimated value of gas concentration in the oil (2), at an instant selected from said measuring instants, according to a non-linear function of the values measured at the selected measuring instant and at one or more of the measuring instants preceding the one selected.

2. The method according to claim 1, wherein said plurality of measurements at successive measuring instants are taken in a predetermined measuring time interval within which the measurements can be ordered sequentially from a first measurement to a last measurement.

3. The method according to claim 1, wherein the successive measuring instants are spaced at predetermined time intervals.

4. The method according to claim 2, comprising, after at least one of the measurements following the first, a step of comparing the value of that measurement and at least one of the preceding values of the plurality of measured values, the step of deriving the estimated value of the gas concentration in the oil (2) corresponding to that measurement being performed in a mode selected according to said comparing step from the following alternatives:
- the calculation according to a non-linear function of the values measured at the selected measuring instant and at one or more of the measuring instants preceding the one selected, or
- a simplified calculation according to a linear function of the value measured at said selected measuring instant.

5. The method according to claim 4, comprising calculating, according to said comparison, the estimated values for all measurements following the first according to a non-linear function of the values measured at the corresponding measuring instant and at the preceding measuring instants.

6. The method according to claim 1, wherein the calculation takes into account the transient of gas permeation through the membrane in the predetermined time interval.

7. A diagnostic method for assessing the insulation condition of an electrical insulating oil (2), comprising the following steps:
- measuring the concentration of a gas dissolved in the oil (2) using a method as in claim 1;
- measuring electrical pulses relating to partial electrical discharges which occur in the oil (2) and which generate said pulses;
- deriving at least one concentration parameter correlated with the gas concentration measured in a predetermined acquisition time interval;
- deriving at least one discharge parameter correlated with the partial discharges measured substantially concurrently with said acquisition time interval;
- deriving a diagnostic indication about the insulation condition of the electrical apparatus (3) according to the derived values of the combined concentration and discharge parameters.

8. The method according to claim 7, wherein the step of deriving the diagnostic indication comprises the following steps:
- preparing a database containing reference values of predetermined indicators relating to a data set comprising at least said concentration and discharge parameters, said reference values being characteristic of predetermined categories of sources that generate the partial discharges and/or the gas dissolved in the oil;
- comparing a data set composed of derived values of the concentration and discharge parameters with the data in the database in order to assign said data set to one or more of said source categories, thereby identifying the type of source that generates the partial discharges and/or the gas dissolved in the oil.

9. The method according to claim 8, wherein the electrical apparatus is a transformer and the predetermined categories of sources that generate the partial discharges and/or the gas dissolved in the oil comprise one or more of the categories from the following list:
- overheating of the transformer;
- electric arcing in a core of the transformer;
- defects in paper insulation of the transformer;
- electrical discharges produced in the oil by a high voltage electrode of the transformer;
- electrical discharges in poorly impregnated zones inside the transformer;
- oil bubbles;
- discharges produced along an outside surface of the transformer insulation.

10. A device for deriving the concentration of a gas dissolved in an electrical insulation oil (2), comprising:
- a membrane (5) permeable to the gas, interposed between a container (7) of the oil and a measuring chamber (4) that receives a part of the gas through the membrane (5);
- a sensor (6) mounted in the measuring chamber (4) to measure a value of the gas concentration in the measuring chamber (4);
- processing means (9) connected to the sensor (6) to derive an estimated value of gas concentration in the oil (2) according to the value measured in the measuring chamber (4), characterized in that the processing means (9) are designed to take, at successive measuring instants, a plurality of measurements of the values of gas concentration in the measuring chamber, and to calculate the estimated value of gas concentration in the oil (2), at an instant selected from said measuring instants, according to a non-linear function of the values measured at the selected measuring instant and at one or more of the measuring instants preceding the one selected.

11. The device according to claim 10, comprising a timer, the processing means (9) being connected to the timer for taking the plurality of measurements at successive measuring instants in a predetermined measuring interval within which the measurements can be ordered sequentially from a first measurement to a last measurement.

12. A diagnostic apparatus (11) for assessing the insulation condition of an electrical insulating oil, comprising
- a device (1) for measuring the concentration of a gas dissolved in the oil (2), according to claim 10;
- a module (10) for measuring electrical pulses relating to partial electrical discharges which occur in the oil (2) and which generate said pulses;
- a processing unit (12) connected to the device (1) and to the module (10) for measuring the partial discharges and designed to derive at least one concentration parameter correlated with the gas concentration measured in a predetermined acquisition time interval and at least one discharge parameter correlated with the partial discharges measured during the same acquisition time interval and to derive a diagnostic indication about the insulation condition of the electrical apparatus according to the derived values of the combined concentration and discharge parameters.

* * * * *